US005277557A

United States Patent [19]
Cooper

[11] Patent Number: 5,277,557
[45] Date of Patent: Jan. 11, 1994

[54] HAND-HELD AND HAND-OPERATED VACUUM PUMP

[76] Inventor: Richard N. Cooper, One Jefferson Pkwy, Apt. 25, Lake Oswego, Oreg. 97035

[21] Appl. No.: 3,102

[22] Filed: Jan. 11, 1993

[51] Int. Cl.$^5$ .............................................. F04B 23/00
[52] U.S. Cl. .................................. 417/440; 417/305; 417/569; 606/123
[58] Field of Search ............... 417/305, 306, 307, 308, 417/434, 440, 461, 467, 470, 566, 569; 604/902; 606/122, 123

[56] References Cited

U.S. PATENT DOCUMENTS

| | | | |
|---|---|---|---|
| 3,612,722 | 10/1971 | Neward | 417/305 |
| 3,794,044 | 2/1974 | Vennard et al. | 606/123 |
| 4,565,506 | 1/1986 | Williams | 417/440 |
| 4,775,302 | 10/1988 | Neward | 417/440 |
| 4,806,084 | 2/1989 | Neward | 417/440 |
| 4,954,054 | 9/1990 | Neward | 417/440 |
| 5,011,381 | 4/1991 | Neward | 417/440 |

FOREIGN PATENT DOCUMENTS 3535055 2/1987 Fed. Rep. of Germany ...... 606/123

Primary Examiner—Richard A. Bertsch
Assistant Examiner—Alfred Basichas
Attorney, Agent, or Firm—Marger, Johnson, McCollom & Stolowitz

[57] ABSTRACT

The invention is directed to a hand-operated vacuum pump and more specifically, a hand-held and hand-operated vacuum pump for obstetrical use incorporating an improved vacuum regulation system. The hand-held and hand-operated vacuum pump comprises a cylinder, having a piston located therewithin. The piston is movable between extended and retracted positions by a hand-operated lever. There is a first passage extending into the cylinder from an external space to be evacuated. The space is defined by the scalp of a baby and a vacuum cranial bell fitted thereon. A second passage connects this intermediate chamber with the cylinder through a first valve, preferably a one-way valve located in the cylinder head. A third passage connects the intermediate chamber to a second valve which automatically controls the maximum vacuum in the external space. A fourth passage from the intermediate chamber is a vacuum adjustment valve.

37 Claims, 2 Drawing Sheets

HAND-HELD AND HAND-OPERATED VACUUM PUMP

BACKGROUND OF THE INVENTION

The present invention is, broadly, a hand-operated vacuum pump and more specifically, a hand-held and hand-operated vacuum pump for obstetrical use incorporating an improved vacuum regulation system.

For several reasons, hand-held vacuum pumps have, in recent years, come to be more widely used than heretofore in delivery rooms. Chief among these is to assist, in combination with a cranial vacuum bell, in a difficult birth, whereby the assisting physician can more easily maneuver the baby's head, without resort to forceps, to better present it for an easier birth, and perhaps gently exert withdrawal pressure thereon, with greatly reduced chances of injury thereto. One reason for this is the greater control hand-held vacuum pumps give over the degree of vacuum obtainable, as contrasted with vacuum systems generally available in hospitals. Other reasons include providing a means of removing obstetrical fluids for later use and to remove particulate matter therefrom.

However, there are hazards associated with the use of cranial vacuum bells. The vacuum can be applied to the scalp of an unborn child only for a very limited period without injury thereto, and the times of use are cumulative. Unless the birthing can be accomplished in that period, the use of the vacuum cup must be terminated. Several problems can extend the time of use dangerously, among them being leaks in the vacuum system, caused by particulate matter being drawn into the pump mechanism. Further, vacuum relief valves which reduce the vacuum to zero, require precious time to restore it to its useful levels.

Typical of existing hand-held vacuum pumps is that disclosed by Neward U.S. Pat. No. 3,612,722. Air from the space to be exhausted, typically that defined by the baby's scalp and the cranial bell fitted thereon, enters directly through intermediate passages into the pump cylinder. Particulate matter entrapped in this air could affect any or all of the vacuum gauge, the vacuum relief valve, the vacuum pump mechanism, or the pump exhaust valve. Further, the vacuum release or adjustment valve is a rotary valve, and must be manually operated by thumb and forefinger of the physician. This manually operated vacuum release design requires the physician to use both hands to operate the pump and simultaneously adjust the vacuum, whereas it may be more important for the physician to have a free hand for other purposes connected with the birthing process.

In Williams U.S. Pat. No. 4,565,506, a hand-operated vacuum pump is provided which includes a cylinder, head assembly, and elastic seal member. The cylinder and head assembly define opposing grooves, and the elastic seal member is positioned in the grooves to secure the head assembly to the cylinder. A piston assembly is operative within the cylinder to draw a vacuum within the head assembly. Pump also includes a manually operated vacuum relief valve which is normally maintained in the closed position. The manually operated vacuum relief valve may be opened by depression of a manual release pin. However, as in the above-described Neward patent, this requires the use of both hands to operate the pump and simultaneously adjust the vacuum.

Finally, Neward U.S. Pat. No. 4,806,084 also describes a hand-held vacuum pump including a manually operated vacuum relief valve system. The vacuum release mechanism is said to be operable with a finger of the hand about the handle. However, a careful examination of the distance from the handle 102 to the relief valve mechanism 400 raises doubts as to ability of a physician to maintain a grip on handle 102 while manually operating relief valve mechanism 400.

SUMMARY OF THE PRESENT INVENTION

Applicants have recognized that none of the prior art devices provide the utmost protection against injury for an infant during the birthing process using a hand-held and hand operated vacuum pump. Instead, all of the above prior art vacuum pumps control vacuum release rely solely on the use of manually operated vacuum relief valves which are performed by the user. In the use of hand-held and hand operated vacuum pumps, the degree of vacuum employed must be kept within predetermined limits, and for a limited cumulative time, in order to avoid traumatizing the baby's scalp and/or drawing it into the cranial cup. During use of a prior art vacuum pump, a physician must manually and precisely adjust the vacuum until the requisite level is reached while carefully watching the vacuum gauge. However, it has been observed by applicants that if the physician's attention becomes confined to the delivery process during the rigors of childbirth, as it often is, the degree of vacuum imparted by the pump to the external space formed by the interior of the vacuum bell surrounding the infant's head can inadvertently exceed maximum prescribed safety limits. This can result in injury to the infant. Manufacturers and users of these prior art vacuum pumps have heretofore not recognized this serious deficiency in the design of such systems.

Applicants have determined that a hand-held, hand-operated vacuum pump should include means for insuring that the degree of vacuum imparted to the head of an infant during delivery (typically using a vacuum bell or like apparatus) does not exceed a predetermined maximum limit. In this way, the above-described injury problems associated with inadvertently applied excess vacuum can be avoided. This can be accomplished by providing vacuum release means in the vacuum pump which are preset at a predetermined maximum degree of vacuum. When the vacuum imparted to the infant during delivery reaches this predetermined maximum level, any excess vacuum will be automatically relieved from within the confines of the vacuum pump. The delivery process will then continue to be conducted at or below the predetermined maximum vacuum level and without causing injury to the child during the birth process.

The hand-held and hand-operated vacuum pump which incorporates the invention comprises a cylinder, having a piston located within the cylinder, the piston being movable between extended and retracted positions. The piston is slidably and reciprocatively operative therein by means of a hand-operated lever. There are means defining a first passage extending into the cylinder from an external space to be evacuated, e.g., the space being defined by the scalp of a baby and a vacuum cranial bell fitted thereon. A second passage connects this intermediate chamber with the cylinder through a first valve, preferably a one-way valve located in the cylinder head. A third passage connects the intermediate chamber to a second valve, which automatically controls the maximum vacuum in the external space, and a fourth passage from the intermediate chamber connects to a third valve which is a vacuum adjustment valve.

The vacuum is created by squeezing a lever operable by the user, particularly the single hand of the user, for reciprocatively operating the piston between the extended and retracted positions thereby evacuating gases from the external space and creating a partial vacuum therein. More specifically, the hand-operated lever and thereby retracting the piston, partially evacuating the space between the cylinder head and the piston, opening the first valve and withdrawing air from the space to be evacuated. The first valve maintains the partial vacuum in the external space when the piston is in a retracted position. When the piston is returned to its rest position, by a spring or other resilient means, it closes the first valve and opens another valve, typically another one-way valve, thereby pushing the evacuated air into the atmosphere.

The second valve is design so that it is in communication with the external space and has a predetermined maximum vacuum limit. The second valve is automatically operable to reduce the vacuum in the external space when the degree of vacuum therein exceeds a predetermined maximum limit. In this way, the second valve controls the maximum degree of vacuum in the external space during the birthing process without conducting any one of manual and visual operations with respect to the vacuum pump by the user. The second valve is typically automatically operable to reduce the vacuum in the external space, when said vacuum exceeds said predetermined maximum limit, to an amount substantially equal to the predetermined maximum limit. Preferably, the second valve comprises a vacuum limit relief valve, typically including a valve assembly including a ball and spring arrangement. More preferably, the second valve comprises a second valve body defining a second valve chamber in communication with the external space; a relief passageway in communication with the second valve chamber and the external space; a valve assembly located within said chamber which is movable between an open position in which the relief passageway is at least partially open and a closed position in which the relief passageway is substantially closed, the valve assembly being in the open position for reducing said vacuum within the external space through the relief passageway when the amount of said vacuum exceeds said predetermined limit, and the valve assembly being in the closed position for maintaining the vacuum within said external space so that it is not passed through the relief passageway when the amount of the vacuum does not exceed the predetermined limit.

The incrementally adjustable third valve in communication with said external space, and operable by the single hand of the user for precisely controlling the entry of air into said external space thereby controlling and incrementally reducing the vacuum in said external space without requiring complete re-evacuation of said external space each time said second valve if opened. The means for operating said third valve typically comprises finger control means operable by the single hand of the user, and preferably these finger control means comprises a trigger. Preferably, the shaft is moved sideways from its normal axial position when the finger control means is actuated so that one side of the valve head is moved from the valve seat and air is admitted into the evacuated space. In the preferred form of this invention, the shaft is long relative to diameter of the valve head, so that the amount of air admitted into the external space can be precisely controlled and thereby controlling with precision the degree of vacuum in the evacuated space. Thus, the third valve is preferably a tilting valve wherein one side of the valve head is lifted from the valve seat for admitting air into the evacuated space.

DETAILED DESCRIPTION OF THE PRESENT INVENTION

Figure 1:
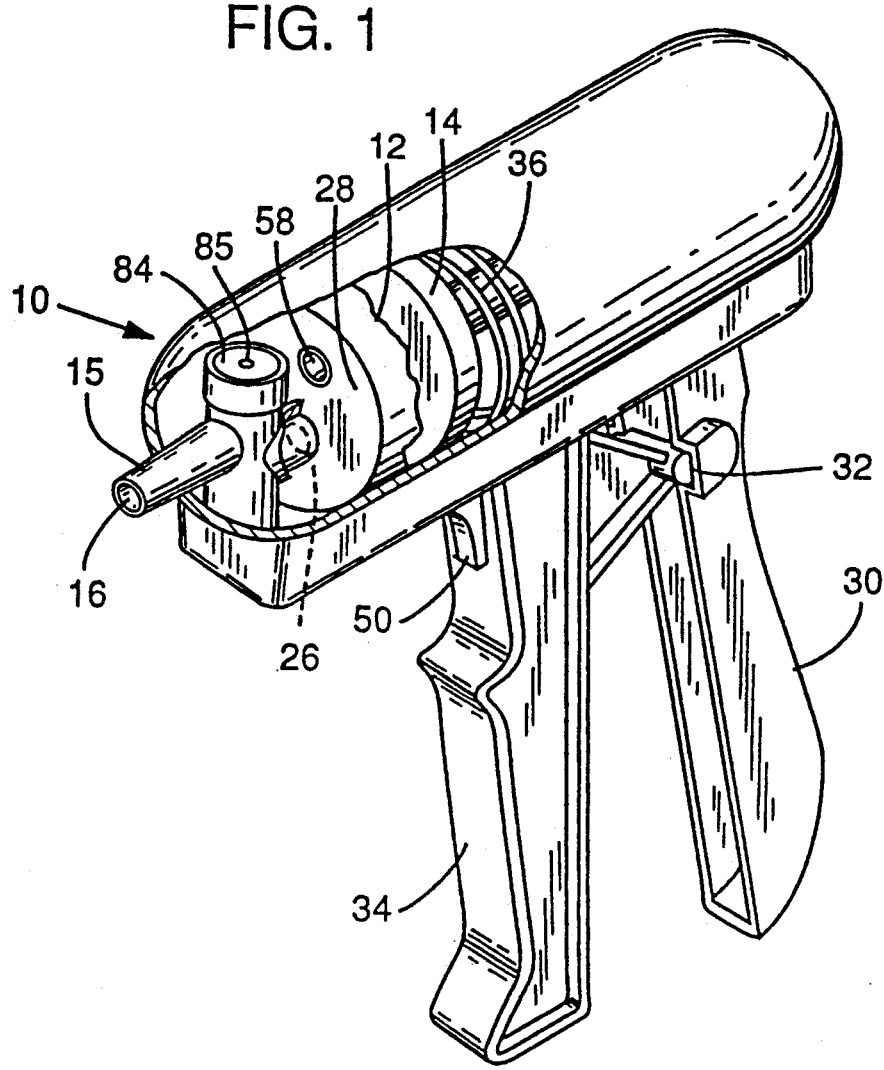
FIG. 1 is a perspective view of the vacuum pump 10 incorporating the present invention, with the major vacuum producing components disclosed in cut-away view.
Figure 1A:
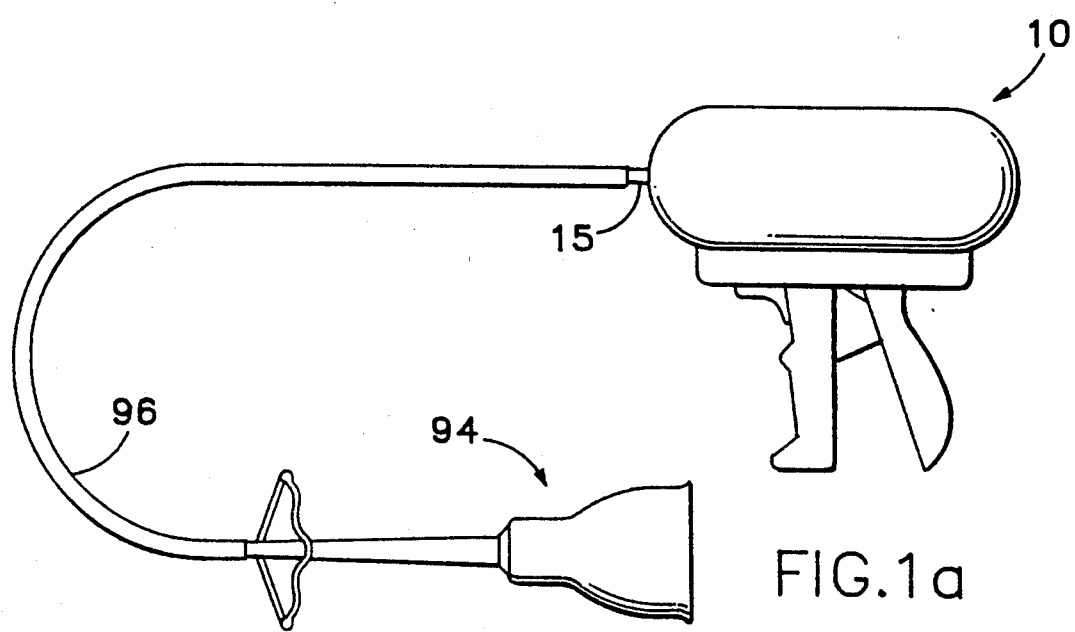
FIG. 1a is a bell-shaped cranial cup and flexible tubing which connects to vacuum pump 10.
Figure 2:
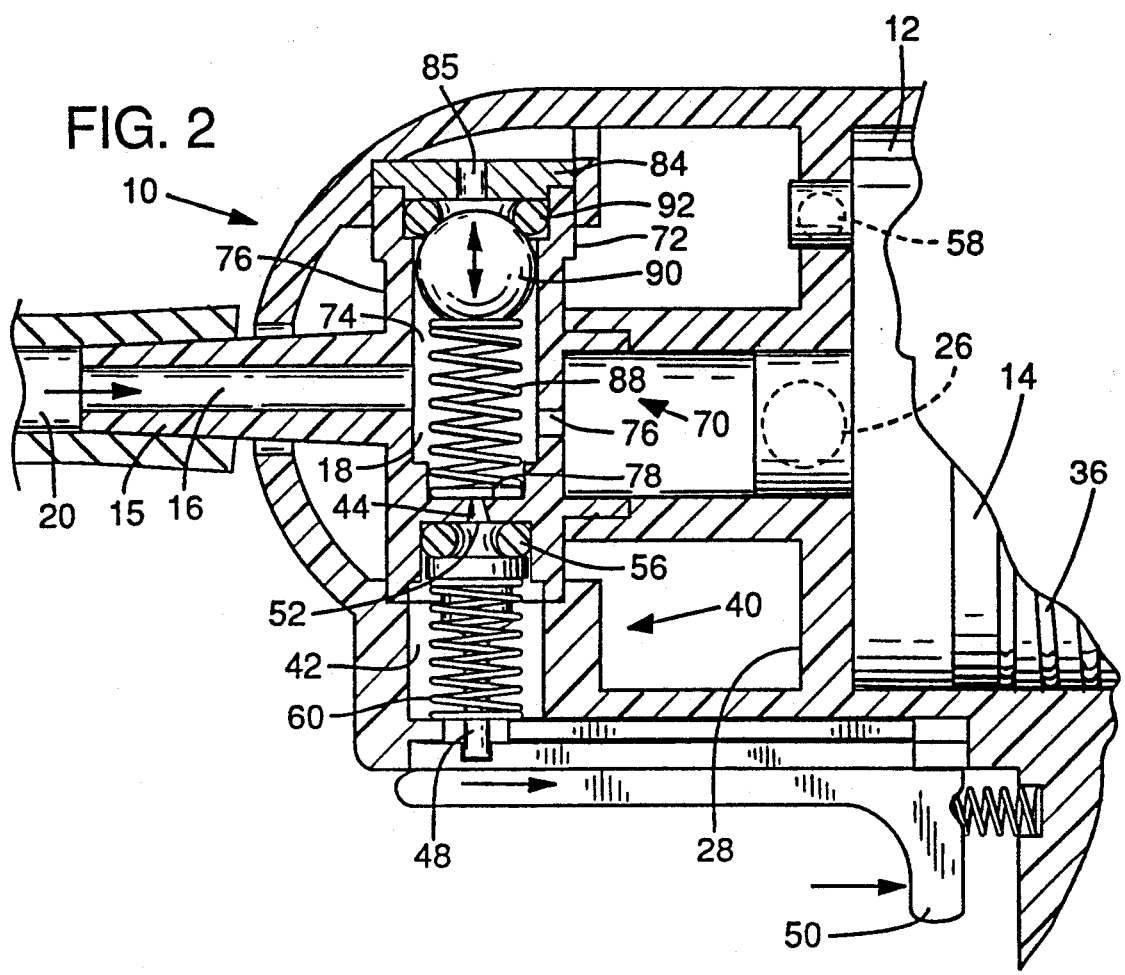
FIG. 2 is an enlarged cross-sectional view of the valve 70 portion of vacuum pump 10.

Turning now to FIGS. 1 & 2, we see hand-held and hand-operative vacuum pump 10 having cylinder 12, piston 14 operative in said cylinder, and first passage 16 located within stem 15 connecting intermediate chamber 18 with external space 20. Passageway 76 connects external space 20 and chamber 18 with cylinder 12 through first one-way valve 26, preferably located in cylinder head 28 of cylinder 12. Hand-operated lever 30 is attached to piston 14 via fulcrum 32 on handle 34, and resilient means 36, typically a cylindrical spring, fits between the backside of piston 14 at the opposite end of cylinder 12 from cylinder head 28. Valve 58 is a one-way valve. It is located preferably in cylinder head 28.

Valve 40 is located in passage 42 between the atmosphere and chamber 18, and is also connected by passageway 44 to vacuum limit relief valve 70. Moreover, Valve 40 and vacuum limit relief valve 70 are ultimately connected to external space 20 through chamber 18 via passageway 16.

Valve 40 includes shaft 48, operatively connected to finger control means (or trigger) 50. Valve 40 includes valve seat 52, valve head 54, seal means 56 between head 54 and seat 52, and spring 60 which is biased against head 54 and the floor of chamber 42. Shaft 48 projects axially from head 54, and is long with respect to the diameter thereof. Trigger means 50 is operatively related to shaft 48 to move it sideways from its normal axial location and thereby lift one side of head 54 from seat 52.

Figure 3:
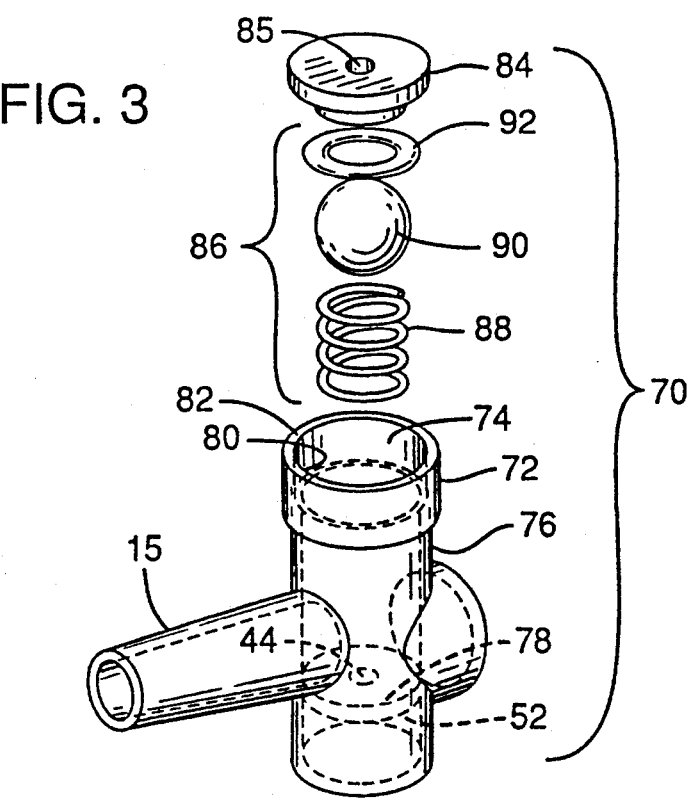
FIG. 3 is a exploded perspective view in cross-section of the valve 70.

The degree of vacuum in space 20 must be kept within strict limits in order to avoid traumatizing the baby's scalp and/or drawing it into the cranial cup 94. To this end, the physician can employ the vacuum pump 10 including vacuum limit relief valve 30 (see FIGS. 2 & 3) without concern as to whether to the degree of actual vacuum because vacuum pump 10 as designed herein does not permit the vacuum in space 20 to exceed the maximum vacuum limit. Vacuum limit relief valve 70 comprises a valve body 72 which defines an internal chamber 74 including a peripheral wall section 76 and a floor section 78. At one end of wall section 76 is an open top 80 defined by a peripheral end 82. Open top 80 is closed off by inserting a plug cap 84 having an aperture 85 therein. Plug cap 84 including aperture 85 is supported within peripheral end 82 and is in communication with passageway 44. Passageway 44 is in turn is in communication with external space 20 through intermediate chamber 18 and first passageway 16. Vacuum limit relief valve 70 includes a valve assembly 86 comprising a spring member 88, typically a coil spring of predetermined tension, a ball bearing 90 and an O-ring 92. The cross-sectional diameter of spring member 88 is sized to snugly fit within the confines of internal chamber 74. The sum of the longitudinal dimension of spring member 88 and the diameter of ball bearing 90 are sized so that together they are greater than the longitudinal dimension of the internal chamber 74. Therefore, when the valve assembly 86 is located within the confines of internal chamber 74, and the plug cap 84 is moved into place onto peripheral end 82 by depressing the spring member 88, ball bearing 90 is urged against plug cap 84 and seats within O-ring 92 firmly pressing against plug cap 84 within orifice 85. This maintains a good vacuum seal in the system by preventing the degree of vacuum Within external space 20 from being relieved through orifice 85. O-ring 92 is employed to fit on the top of the ball bearing 90 for maintaining the valve assembly 86 in seated position within orifice 85.

Vacuum limit relief valve 70 has a predetermined maximum vacuum limit. Valve 70 is automatically operable to reduce the vacuum in external space 20 if it exceeds this predetermined maximum limit. In vacuum pump 10, spring member 88 has a predetermined tension. The value of the predetermined tension of the spring member 88 is selected so that the vacuum limit relief valve 70 will operate to relieve the vacuum in external space 20 when the degree of vacuum therein exceeds the predetermined maximum vacuum limit. Then, the spring member 88, and in turn ball bearing 90, are moved away from O-ring seat 92 and plug cap 84 when the maximum vacuum limit is exceeded, so that ball bearing 90 is unseated from within orifice 85, and the vacuum is relieved through orifice 85.

Valves 26 and 58 can be any type of valve that operates automatically as the pump is operated. Preferably, they are a sterilizable valve such as a butterfly valve or the like, but are not limited thereto. Valve 70 can be of any type that operates automatically to relieve the vacuum in external space 20 when it exceeds a predetermined maximum limit. Preferably, valve 70 is a sterilizable vacuum limit relief valve or the like, but is not limited thereto.

In the operation of pump 10, a bell-shaped cranial vacuum cup 94, which connects to stems 15 by flexible tubing 96, is inserted in the birth canal by the attending physician and placed on the crown of an unborn baby's head therein. The cranial vacuum cup and the baby's scalp define space 20 which is to be evacuated. While holding the cranial cup in place, the physician grips handle 34 of pump 10 and squeezes lever 30, which retracts piston 14 from cylinder head 28, and creating a partial vacuum in the space thereby enlarged. This opens first one-way valve 26, partially exhausting gases from space 20, first passage 16, chamber 18, and first valve 26 into cylinder 12.

When the pressure on lever 30 is released, resilient means 36 operates to restore piston 14 to rest position, and one-way valve 58 opens to exhaust the evacuated gases into the atmosphere. Successive pumping of lever 30, with the consequent retractions and restorations of piston 14 progressively reduce the amount of gas in space 20, and thereby increases the vacuum therein, permitting the physician to assist labor by gently maneuvering the baby's head for better presentation and an easier birth.

Valve 40 operates as follows, as seen more clearly in FIG. 2. A valve head 54 is seated on valve seat 52, with shaft 48 extending axially therefrom. O-ring 56 is preferably inserted between valve head 54 and seat 52 to improve the seating. Spring 60 keeps head 54 firmly pressed against seat 52 or O-ring 56, maintaining a good vacuum seal. When trigger 50 is squeezed, one side of valve head 54 is lifted from the corresponding portion of seat 52 or O-ring 56, permitting air to enter space 20 through passage 44, chamber 18 and passage 16. Because shaft 48 magnifies the lever arm for lifting head 54 from valve seat 52, it permits precise control over the amount of air admitted into space 20, and thus does not require completely re-evacuating space 20 following each time valve 40 is opened, as most valves do.

As for vacuum limit relief valve 70, as described above, in normal operation maximum ball bearing 90 is urged against plug cap 84 and seats within orifice 85 firmly pressing against plug cap 84 within orifice 85. This maintains a good vacuum seal in the system by preventing the degree of vacuum within external space 20 from being relieved through orifice 85. On the other hand, if the maximum vacuum limit is exceeded, ball bearing 90 is moved from within orifice 85 and O-ring seat 92, and the vacuum within external space 20 is relieved through orifice 85.

It will be seen by those skilled in the art that operation of pump 10 to relieve excess vacuum above the maximum vacuum limit during the birthing process without conducting any one of manual and visual operations with respect to the vacuum pump by the user, leaving the physician's hands free for other important tasks.

The terms and expressions which have been employed in the foregoing specification are used therein as terms of description and not of limitation, and there is no intention, in the use of such terms and expressions, of excluding equivalents of the features shown and described, or portions thereof, it being recognized that the scope of the invention is defined and limited only by the claims which follow.

I claim:

1. A hand-held, hand-operated vacuum pump operable by a user during the birthing process, comprising
   a cylinder;
   a piston, located within said a cylinder, which is movable between extended and retracted positions;
   means defining a first passage extending into said cylinder from an external space to be evacuated, said external space being defined by the scalp of a baby and a vacuum cranial bell fitted thereon;
   a lever operable by the single hand of the user for reciprocatively operating said piston between said extended and retracted positions thereby evacuating gases from said external space and creating a partial vacuum therein;
   a first valve for maintaining said partial vacuum in said external space when said piston is in a retracted position; and
   a second valve having a predetermined maximum vacuum limit, in communication with said external space, which is automatically operable to reduce the vacuum in said external space when said vacuum exceeds said predetermined maximum limit, thereby controlling the maximum degree of vacuum in said external space during said birthing process without conducting any one of manual and visual operations with respect to the vacuum pump by the user.

2. The vacuum pump of claim 1, wherein said second valve is automatically operable to reduce the vacuum in said external space, when said vacuum exceeds said predetermined maximum limit, to an amount substantially equal to the predetermined maximum limit.

3. The vacuum pump of claim 1, wherein said second valve comprises a vacuum limit relief valve.

4. The vacuum pump of claim 1, wherein said second valve comprises a second valve body defining a second valve chamber in communication with said external space; a relief passageway in communication with said second valve chamber and said external space; a valve assembly located within said chamber which is movable between an open position in which said relief passageway is at least partially open and a closed position in which said relief passageway is substantially closed, said valve assembly being in said open position for reducing said vacuum within said external space through said relief passageway when the amount of said vacuum exceeds said predetermined limit, and said valve assembly being in said closed position for maintaining the vacuum within said external space so that it is not pass through said relief passageway when the amount of said vacuum does not exceed said predetermined limit.

5. The vacuum pump of claim 1, wherein said valve assembly includes a ball and spring arrangement.

6. The pump of claim 1, which further includes an incrementally adjustable third valve in communication with said external space, and operable by the single hand of the user for precisely controlling the entry of air into said external space thereby controlling and incrementally reducing the vacuum in said external space without requiring complete re-evacuation of said external space each time said second valve if opened.

7. The pump of claim 6, wherein said means for operating said third valve comprises finger control means operable by the single hand of the user.

8. The vacuum pump of claim 7, wherein said finger control means comprises a trigger.

9. The vacuum pump of claim 7, wherein said shaft is moved sideways from it normal axial position when said finger control means is actuated so that one side of said valve head is moved from the valve seat and air is admitted into the evacuated space.

10. The vacuum pump of claim 7, wherein said shaft is long relative to diameter of said valve head, so that the amount of air admitted into the external space can be precisely controlled and thereby controlling with precision the degree of vacuum in the evacuated space.

11. The vacuum pump of claim 7, wherein said second valve a tilting valve wherein one side of said valve head is lifted from said valve seat for admitting air into said evacuated space.

12. A birthing-assistance system, comprising
a hand-operated, hand-held vacuum pump including a cylinder;
a bell-shaped cranial or vacuum cup means for assisting in the delivery of a baby which is connected to said hand-held vacuum pump and in communication with the interior of said cylinder, said hand-held vacuum pump including
a cylinder;
a piston, located within said a cylinder, which is movable between extended and retracted position;
means defining a first passage extending into said cylinder from an external space to be evacuated, said external space being defined by the scalp of a baby and a vacuum cranial bell fitted thereon;
a lever operable by the single hand of the user for reciprocatively operating said piston between said extended and retracted positions thereby evacuating gases from said external space and creating a partial vacuum therein;
a first valve for maintaining said partial vacuum in said external space when said piston is in a retracted position; and
a second valve having a predetermined maximum vacuum limit, in communication with said external space, which is automatically operable to reduce the vacuum in said external space when said vacuum exceeds said predetermined maximum limit, thereby controlling the maximum degree of vacuum in said external space during said birthing process without conducting any one of manual and visual operations with respect to the vacuum pump by the user.

13. The vacuum pump of claim 12, wherein said second valve is automatically operable to reduce the vacuum in said external space, when said vacuum exceeds said predetermined maximum limit, to an amount substantially equal to the predetermined maximum limit.

14. The vacuum pump of claim 12, wherein said second valve comprises a vacuum limit relief valve.

15. The vacuum pump of claim 12, wherein said second valve comprises a second valve body defining a second valve chamber in communication with said external space; a relief passageway in communication with said second valve chamber and said external space; a valve assembly located within said chamber which is movable between an open position in which said relief passageway is at least partially open and a closed position in which said relief passageway is substantially closed, said valve assembly being in said open position for reducing said vacuum within said external space through said relief passageway when the amount of said vacuum exceeds said predetermined limit, and said valve assembly being in said closed position for maintaining the vacuum within said external space so that it is not passed through said relief passageway when the amount of said vacuum does not exceed said predetermined limit.

16. The vacuum pump of claim 12, wherein said valve assembly includes a ball and spring arrangement.

17. The pump of claim 12, which further includes an incrementally adjustable third valve in communication with said external space, and operable by the single hand of the user for precisely controlling the entry of air into said external space thereby controlling and incrementally reducing the vacuum in said external space without requiring complete re-evacuation of said external space each time said second valve is opened.

18. The system of claim 12, wherein means for operating said incrementally adjustable valve comprises finger control means operable by the single hand of the user.

19. The system of claim 12, wherein said incrementally adjustable valve further includes a valve seat; a valve head sealingly seated on said valve seat; and a shaft projecting axially from said head and operatively connected to said finger control means, said finger control means including means for moving said shaft from its normal axial position and thereby separating said valve head from its sealingly seated position on said valve seat.

20. The system of claim 18, wherein said finger control means comprises a trigger.

21. The system of claim 19, wherein said shaft is moved sideways from its normal axial position when said finger control means is actuated so that one side of said valve head is moved from the valve seat and air is admitted into the evacuated space.

22. The system of claim 19, wherein said shaft is long relative to diameter of said valve head, so that the amount of air admitted into the external space can be precisely controlled and thereby controlling with precision the degree of vacuum in the evacuated space.

23. The system of claim 19, wherein said incrementally adjustable valve comprises a tilting valve wherein one side of said valve head is lifted from said valve seat for admitting air into said evacuated space.

24. The system of claim 19, wherein said valve head and valve seat are located external to said chamber.

25. A method for operating a hand-held, hand-operated vacuum pump by a user during the birthing process, which comprises:
providing a hand-operated, hand-held vacuum pump including a cylinder, and a bell-shaped cranial vacuum cup means for assisting in the delivery of a baby which is connected to said hand-held vacuum pump and in communication with the interior of said cylinder, said hand-operated, hand-held vacuum pump including a valve having a predetermined maximum vacuum limit, in communication with said external space, which is automatically operable to reduce the vacuum in said external space when said vacuum exceeds said predetermined maximum limit;
inserting said bell-shaped cranial vacuum cup means in a birth canal of a birthing mother and placing said bell-shaped cranial cup means on the scalp of an unborn baby's head, the bell-shaped cranial vacuum cup means and the scalp of the baby together defining an external space;
creating a partial vacuum in said external space by user operating said hand-held, hand-operated vacuum pump, thereby evacuating gases from said external space and permitting the user to assist the birthing process by maneuvering the baby's head for better presentation and an easier birth; and
automatically controlling the maximum degree of vacuum in said external space during said birthing process to avoid traumatizing the baby's scalp and/or drawing it into the cranial cup without conducting either one of any manual and visual operations with respect to the vacuum pump by the user.

26. The method of claim 25, which further includes the step of providing an incrementally adjustable valve in communication with said external space; precisely controlling the degree of vacuum within said external space by operating the incrementally adjustable valve using the single hand of the user for precisely controlling the entry of air into said external space thereby controlling and incrementally reducing the vacuum in said external space without requiring complete re-evacuation of said external space each time said incrementally adjustable valve is opened, and leaving the other hand of the user available for performing different important tasks required during the birthing process.

27. The method of claim 26, which includes the step of operating said incrementally adjustable valve with finger control means operable by the single hand of the user.

28. The method of claim 27, which includes the step of providing said incrementally adjustable valve including a valve seat, a valve head sealingly seated on said valve seat, and a shaft projecting axially from said head and operatively connected to said finger control means, and moving said shaft with said finger control means from its normal axial position and thereby separating said valve head from its sealingly seated position on said valve seat.

29. The method of claim 27, which includes the step of providing finger control means which comprises a trigger.

30. The method of claim 28, which includes the step of moving said shaft sideways from it normal axial position when said finger control means is actuated so that one side of said valve head is moved from the valve seat and air is admitted in the external space.

31. The method of claim 28, which includes the step of providing a shaft which is long relative to diameter of said valve head and admitting an amount of air into the external space which can be precisely controlled, and thereby controlling with precision the degree of vacuum in the external space.

32. The method of claim 28, which includes the step of providing a tilting valve as the incrementally adjustable valve, and admitting air into said external space by lifting one side of said valve head from said valve seat.

33. The method of claim 28, which includes the step of locating said valve head and valve seat external to said chamber.

34. The method of claim 25, wherein said automatic control of the maximum limit of said vacuum is operable to reduce the vacuum in said external space to an amount substantially equal to the predetermined maximum limit when said vacuum exceeds said predetermined maximum limit.

35. The method of claim 25, wherein said maximum degree of vacuum is automatically controlled by a vacuum limit relief valve.

36. The method of claim 35, wherein said vacuum limit relief valve comprises a valve body defining a valve chamber in communication with said external space; a relief passageway in communication with said valve chamber and said external space; a valve assembly located within said valve chamber which is movable between an open position in which said relief passageway is at least partially open and a closed position in which said relief passageway is substantially closed, said valve assembly being in said open position for reducing said vacuum within said external space through said relief passageway when the amount of said vacuum exceeds said predetermined limit, and said valve assembly being in said closed position for maintaining the vacuum within said external space so that it is not passed through said relief passageway when the amount of said vacuum does not exceed said predetermined limit.

37. The vacuum pump of claim 36, wherein said valve assembly comprises a ball and spring arrangement.

* * * * *